US00PP37853P2

(12) United States Plant Patent
Hartman

(10) Patent No.: US PP37,853 P2
(45) Date of Patent: Nov. 24, 2026

(54) ***CALADIUM* PLANT NAMED 'BLB F-023'**

(50) Latin Name: ***Caladium* X *hortulanum***
Varietal Denomination: BLB F-023

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 19/639,727

(22) Filed: Apr. 6, 2026

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP25,419 P2 * 4/2015 Hartman ..... A01H 6/10
Plt./373

* cited by examiner

*Primary Examiner* — Susan Mccormick Ewoldt
(74) *Attorney, Agent, or Firm* — C. Anne Whealy

(57) ABSTRACT

A new and distinct cultivar of *Caladium* plant named 'BLB F-023', characterized by its upright plant habit and tall in height; dense, leafy and bushy appearance; vigorous growth habit and rapid growth rate; lance-type leaves that have a white-colored background variably mottled with various shades of reddish pink with dark green-colored margins; and petioles that are pinkish brown in color with dark reddish brown-colored streaks.

5 Drawing Sheets

Figure 1:
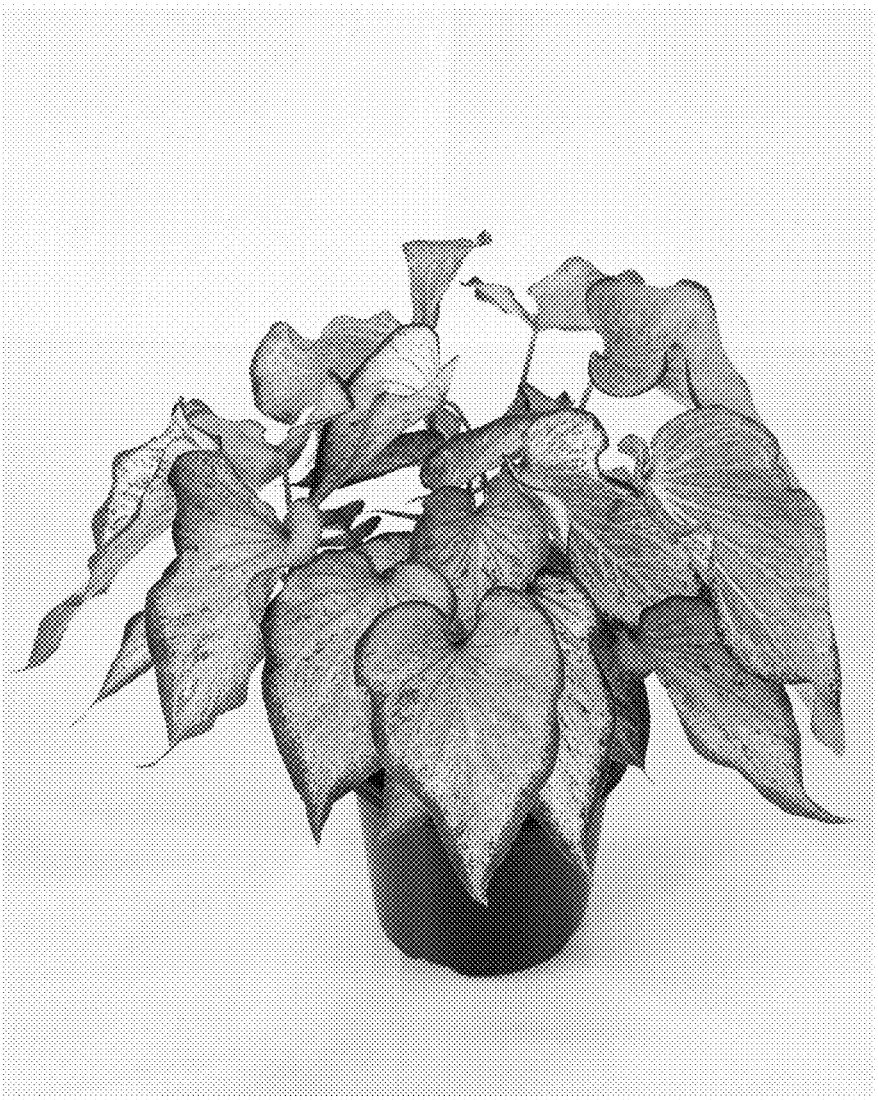

Botanical designation: *Caladium* X *hortulanum*.
Cultivar denomination: 'BLB F-023'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'BLB F-023'.

The objective of the Inventor's breeding program is to create new *Caladium* plants that have uniform plant habit, exceptional container and garden performance and attractive and unique leaf coloration.

The new *Caladium* plant is a naturally-occurring whole plant mutation of *Caladium* X *hortulanum* 'Blushing Bride', disclosed in U.S. Plant Pat. No. 22,213. The new *Caladium* plant was discovered and selected by the Inventor as a single plant within a population of plants of 'Blushing Bride' in a controlled outdoor nursery environment in Zolfo Springs, Florida on Sep. 15, 2022.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since Apr. 15, 2023 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BLB F-023'. These characteristics in combination distinguish 'BLB F-023' as a new and distinct *Caladium* plant:

1. Upright plant habit and tall in height; dense, leafy and bushy appearance.
2. Vigorous growth habit and rapid growth rate.
3. Lance-type leaves that have a white-colored background variably mottled with various shades of reddish pink with dark green-colored margins.
4. Petioles that are pinkish brown in color with dark reddish brown-colored streaks.

Plants of the new *Caladium* differ primarily from plants of the mutation parent, 'Blushing Bride', in the following characteristics:

1. Plants of the new *Caladium* are taller and more upright than plants of 'Blushing Bride'.
2. Plants of the new *Caladium* are more vigorous than plants of 'Blushing Bride'.
3. Plants of the new *Caladium* produce larger tubers than plants of 'Blushing Bride'.
4. Plants of the new *Caladium* produce more leaves and are denser than plants of 'Blushing Bride'.
5. Leaves of plants of the new *Caladium* are lighter in color than leaves of plants of 'Blushing Bride' especially when grown under high light field conditions.

Plants of the new *Caladium* can be compared to plants of *Caladium* X *hortulanum* 'Scarlet Flame', disclosed in U.S. Plant Pat. No. 25,419. In side-by-side comparisons, plants of the new *Caladium* differ primarily from plants of 'Scarlet Flame' in the following characteristics:

1. Plants of the new *Caladium* are taller than and are not as mounding as plants of 'Scarlet Flame'.
2. Plants of the new *Caladium* are more vigorous and grow faster than plants of 'Scarlet Flame'.
3. Leaves of plants of the new *Caladium* have a white-colored background variably mottled with various shades of reddish pink with dark green-colored margins whereas leaves of plants of 'Scarlet Flame' are dark green in color with rose red-colored venation and pink and rose red-colored spots and blotches.
4. Petioles of plants of the new *Caladium* are pinkish brown in color with dark reddish brown-colored streaks whereas petioles of plants of 'Scarlet Flame' are dark green in color densely covered with dark brown-colored streaks and stippling appearing almost black in color.

Plants of the new *Caladium* can be compared to plants of *Caladium* X *hortulanum* 'Tickle Me Pink', disclosed in U.S. Plant Pat. No. 31,061. In side-by-side comparisons, plants of the new *Caladium* differ primarily from plants of 'Tickle Me Pink' in the following characteristics:

1. Plants of the new *Caladium* have more leaves and are denser than plants of 'Tickle Me Pink'.
2. Leaves of plants of the new *Caladium* are smaller than leaves of plants of 'Tickle Me Pink'.
3. Leaves of plants of the new *Caladium* have a white-colored background variably mottled with reddish pink with dark green-colored margins whereas leaves of plants of 'Tickle Me Pink' have dark green-colored margins, rose red venation and interveinal areas that are green, tan green and rose red mosaic.
4. Petioles of plants of the new *Caladium* are pinkish brown in color with dark reddish brown-colored streaks whereas petioles of plants of 'Tickle Me Pink' are green or tan pink in color with darker-colored stippling and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'BLB F-023' grown in a container that has not had its tuber de-eyed prior to planting.

Figure 2:
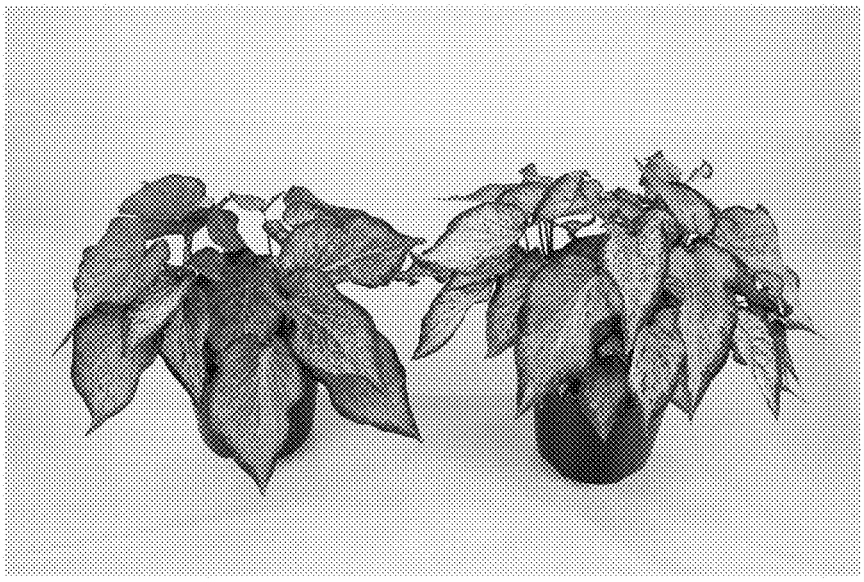

The photograph at the top of the second sheet (FIG. 2) is side perspective view of typical plants of the mutation parent, 'Blushing Bride', (left) and 'BLB F-023' (right).

Figure 3:
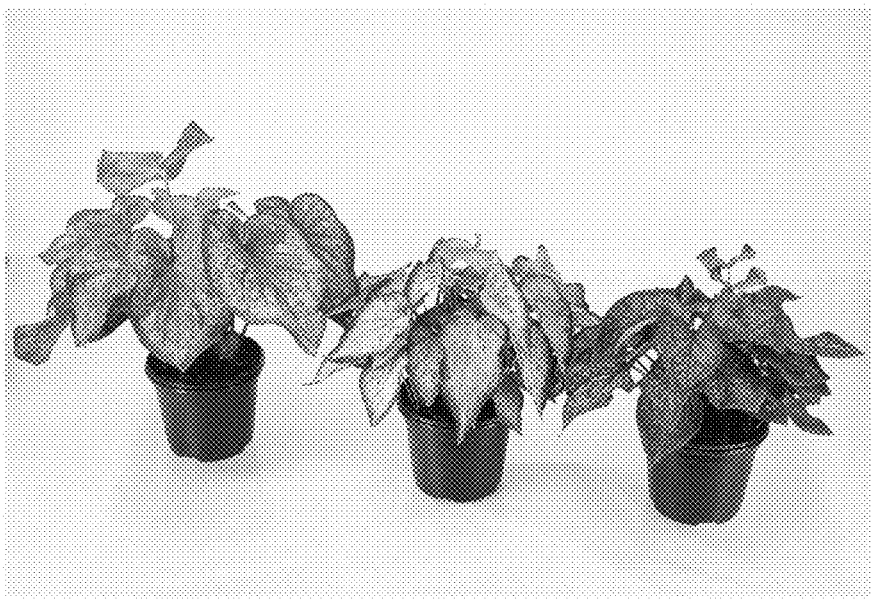

The photograph at the bottom of the second sheet (FIG. 3) is side perspective view of typical plants of 'Tickle Me Pink' (left), 'BLB F-023' (center) and 'Scarlet Flame' (right).

Figure 4:
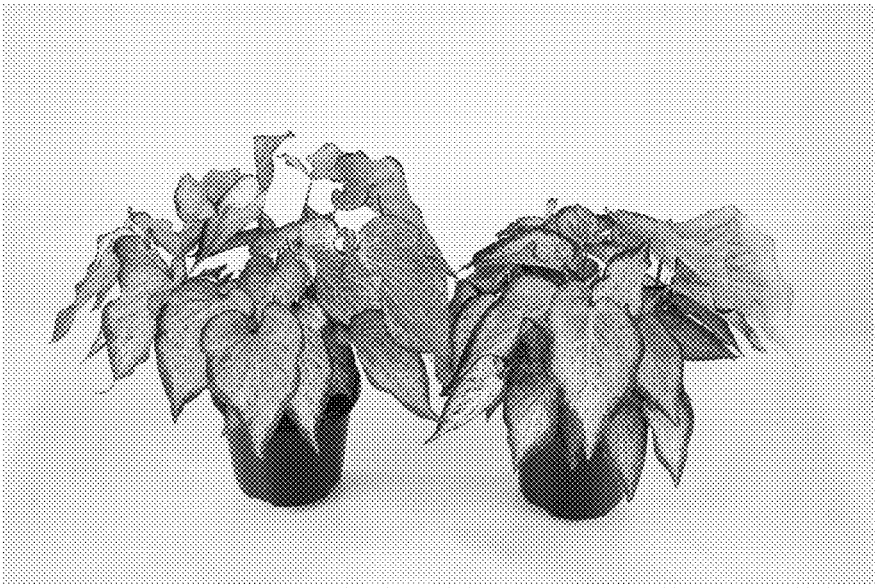

The photograph at the top of the third sheet (FIG. 4) is a comparison view of typical plants of 'BLB F-023' grown in containers, the plant on the left has not had its tuber de-eyed and the plant on the right has had its tuber de-eyed prior to planting.

Figure 5:
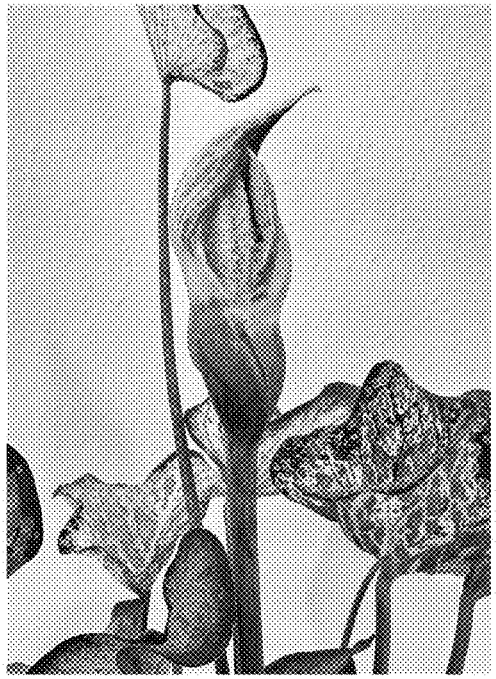

The photograph at the bottom of the third sheet (FIG. 5) is a close up view of a typical inflorescence of 'BLB F-023'.

Figure 6:
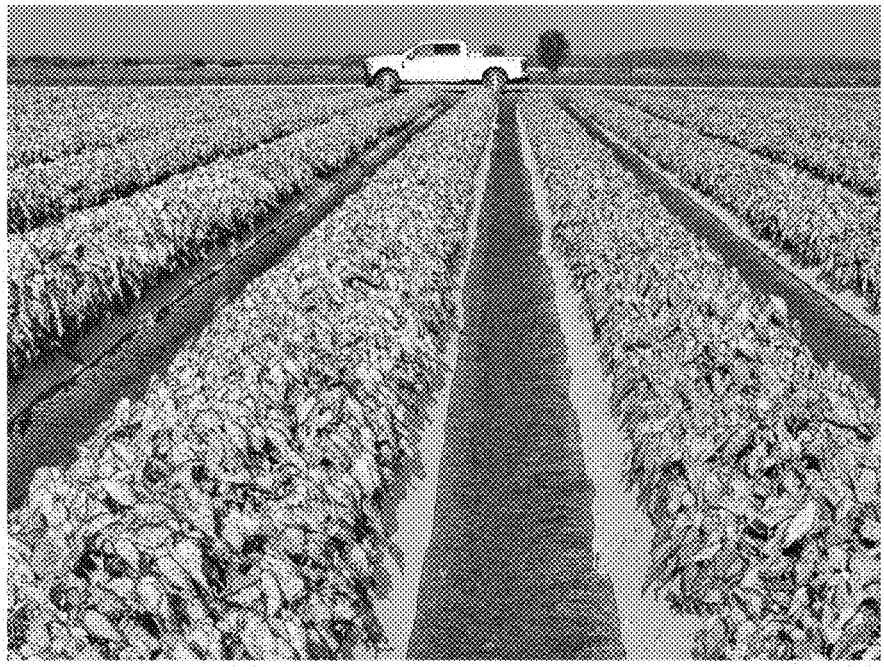

The photograph at the top of the fourth sheet (FIG. 6) is a view of typical field-grown plants of 'BLB F-023' (left) and 'Blushing Bride' (right).

Figure 7:
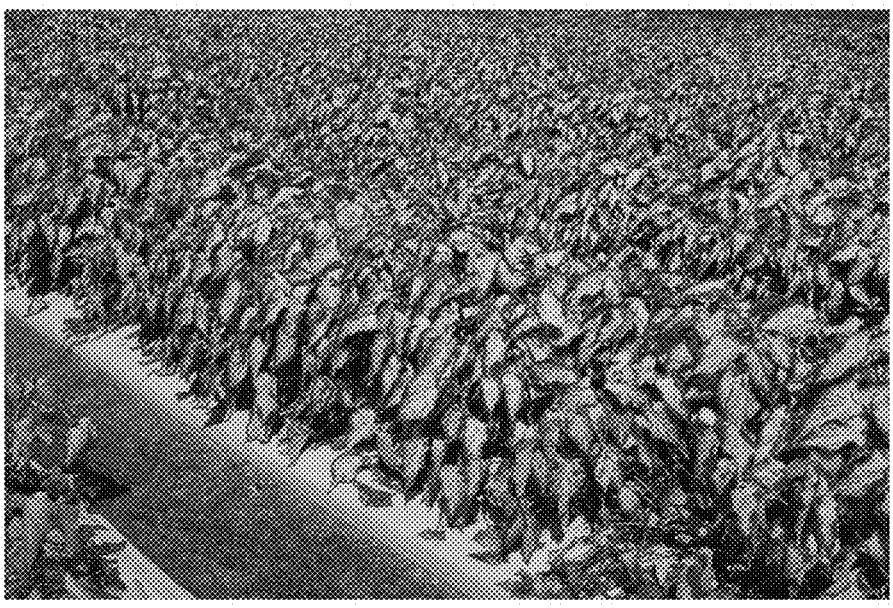

The photograph at the bottom of the fourth sheet (FIG. 7) is a view of a field-grown stand of 'BLB F-023' started from seed pieces.

Figure 8:
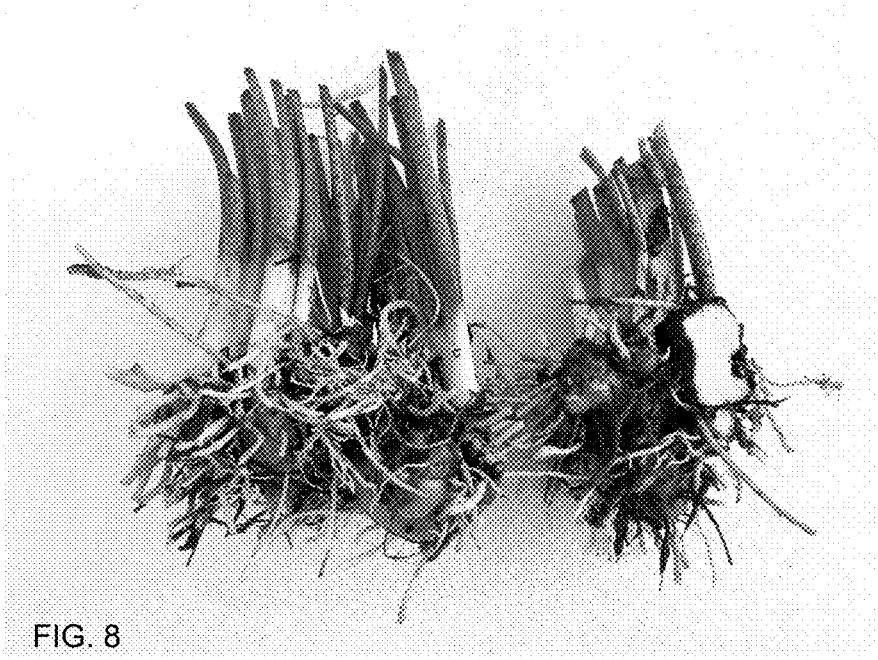

The photograph at the top of the fifth sheet (FIG. 8) is a close-up view of freshly-harvested tubers with roots of 'BLB F-023' (left) and 'Blushing Bride' (right).

Figure 9:
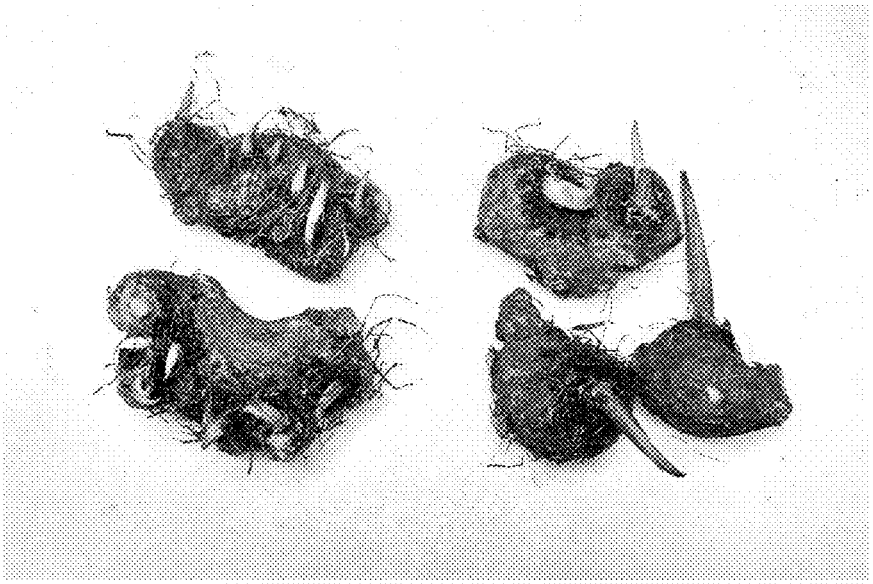

The photograph at the bottom of the fifth sheet (FIG. 9) is a close-up view of typical dry dormant tubers of 'BLB F-023' (left) and 'Blushing Bride' (right).

DETAILED BOTANICAL DESCRIPTION

The aforementioned photographs and following observations and measurements describe plants grown in 15-cm containers in a polypropylene-covered shade house (30% light reduction) in Avon Park, Florida and plants grown in ground beds under full sunlight conditions in an outdoor nursery in Zolfo Springs, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and levels were about 1,300μmol. During the production of the outdoor nursery-grown plants, day temperatures ranged from about 29° C. to 35° C., night temperatures ranged from about 23° C. to 26° C. and under full sunlight conditions. Plants grown in the shade house were about eight weeks old and plants grown in the outdoor nursery were about seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'BLB F-023'.

Parentage: Naturally-occurring whole plant mutation of *Caladium* X *hortulanum* 'Blushing Bride', disclosed in U.S. Plant Pat. No. 22,213.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and branched; individual segments are elliptic or irregular in shape. Height: About 2.6 cm to 3.6 cm. Diameter, largest width: About 4.4 cm to 7.1 cm. Segment height: About 1.8 cm to 2.9 cm. Segment diameter: About 2.6 cm to 2.9 cm. Axillary bud shape: Roughly triangular. Axillary bud height: About 4.5 mm. Axillary bud width: About 3 mm. Texture: Thick, starchy; somewhat brittle. Color: Periderm, freshly-harvested: Close to 199C. Periderm, dried: Close to 200D, N199B and N199C. Epidermis: Close to 159C. Cortical tissue: Close to N155B, 10D and 11D. Axillary buds: Close to 36C. Root description: Relatively thin, fleshy contractile roots with few lateral branches; color, close to N155B, N155C and NN155D; actual color of the roots is dependent on substrate composition, water quality, fertilizer type and formulation, substrate temperature and physiological age of roots; root density, dense.

Plant description:

*Plant type.*—Herbaceous perennial; suitable as a potted plant in containers 15-cm to 25-cm and suitable as a landscape plant in shaded areas.

*Plant and growth habit.*—Upright plant habit; tall in height; dense, leafy and bushy appearance; vigorous growth habit and rapid growth rate; potted plants finish in saleable form in about five to six weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed.*—About 17.5 cm to 21 cm.

*Plant height, from soil level to top of foliar plane, shade house-grown potted plants, tubers not de-eyed.*—About 18 cm to 21 cm.

*Plant height, from soil level to top of inflorescences.*—About 35 cm.

*Plant diameter, shade house-grown potted plants, tubers de-eyed.*—About 27 cm to 30 cm.

*Plant diameter, shade house-grown potted plants, tubers not de-eyed.*—About 25 cm to 29 cm.

*Number of shoots per plant, shade house-grown potted plants, tubers de-eyed.*—About seven to ten develop per #1 tuber.

*Number of shoots per plant, shade house-grown potted plants, tubers not de-eyed.*—About six to nine develop per #1 tuber.

*Cataphylls, shade house-grown potted plants.*—Length: About 4.5 cm to 5.2 cm. Width: About 7 mm. Shape: Narrow, lanceolate to wedge-shaped. Apex: Acute. Base: Sheathing the stem. Texture, outer and inner surfaces: Smooth, glabrous. Color, outer surface: Close to 181D and 177D with stippling and streaks, close to 200A to 200B; fading to N199B to N199C with subsequent development. Color, inner surface: Close to N155D; colors and patterns on outer surface are visible on inner surface.

Leaf description:

*Arrangement and type.*—Alternate; simple; lance-type.

*Length, shade house-grown potted plants, tubers de-eyed.*—About 9.5 cm to 15 cm.

*Length, shade house-grown potted plants, tubers not de-eyed.*—About 10.5 cm to 21.5 cm.

*Width, shade house-grown potted plants, tubers de-eyed.*—About 5.2 cm to 8.5 cm; when flattened, about 6.1 cm to 9.5 cm.

*Width, shade house-grown potted plants, tubers not de-eyed.*—About 6.5 cm to 12.5 cm; when flattened, about 7.3 cm to 14.2 cm.

*Shape.*—Ovate with cordate tendencies.

*Apex.*—Acute to acuminate.

*Base.*—Sagittate, sagittate-peltate or cordate.

*Margin.*—Entire; somewhat wavy with broad undulations.

*Texture and luster, upper surface.*—Smooth, glabrous; dull sheen.

*Texture and luster, lower surface.*—Smooth, glabrous; glaucous in center and around venation, dull sheen.

*Venation pattern.*—Pinnate and palmate.

*Color, shade house-grown potted plants.*—Developing leaves, upper surface: Interveinal areas: Close to 155C, 147A, 147D, and 196C to 196D with spots and blotches, close to 59C. Margins: Close to 147A with narrow marginal edges, close to 183A. Basal notch: Close to 59B. Midvein: Close to 196C to 196D variably tinged with close to 185D. Lateral venation: Close to 196C to 196D variably tinged with close to 184C and 184D. Developing leaves, lower surface: Interveinal areas: Close to 146C, 147B to 147C, N155B and N155C with spots and blotches, close to 59C. Margins: Close to 191A with narrow marginal edges, close to 183A. Basal notch: Close to 59C. Midvein and lateral venation: Close to 197C variably tinged with close to 177D. Fully expanded leaves, upper surface: Interveinal areas: Close to 194D, 137B, 54D, 58D, 59C and 59D. Margins: Close to 147A with narrow marginal edges, close to 183A. Basal notch: Close to 59B. Midvein: Close to 56C and 64D or 145D and 192A. Lateral venation: Close to 56C, 59D and 192C. Fully expanded leaves, lower surface: Interveinal areas: Close to N155B, 56C, 56D and 137D with spots and blotches, close to 59C and 59D. Margins: Close to 191A with variable spots, close to 63B and with narrow marginal edges, close to 183A. Basal notch: Close to 59B. Midvein and lateral venation: Close to N148D and 195B with flecks, close to 147B. Oldest leaves, upper surface: Interveinal areas: Close to 59C and 59D. Margins: Close to 192A, 137A and 147A with spots, close to 59D and with narrow marginal edges, close to 183A. Basal notch: Close to 59B. Midvein: Close to 155C, 56A and 64D. Lateral venation: Close to 59D and 56C. Oldest leaves, lower surface: Interveinal areas: Mostly 59D with darker areas, close to 59C, 56C and 56D. Margins: Close to 191A with variable spots, close to 59C and 59D and with narrow marginal edges, close to 183A. Basal notch: Close to 59B. Midvein and lateral venation: Close to 195B surrounded with close to N155B and N155C.

*Petioles.*—Aspect: Initially upright and straight and leaning outwardly to arching with development; flexible. Length, shade house-grown potted plants, tubers de-eyed: About 10 cm to 16 cm. Length, shade house-grown potted plants, tubers not de-eyed: About 11.4 cm to 16 cm. Diameter, distally, shade house-grown potted plants, tubers de-eyed or not de-eyed: About 2 mm to 3.7 mm. Diameter, proximally, shade house-grown potted plants, tubers de-eyed or not de-eyed: About 4 mm to 5 mm. Texture and luster: Smooth, glabrous; glaucous. Color, shade house-grown potted plants: When developing: Close to 159D with stippling and streaks, close to 200D. Developed: Close to 181D and 177D with stippling and streaks, close to 200A and 200B; just below the leaf junction, close to N170D tinged with close to 182D with faint stippling and streaks, close to 200D. Wing length, shade house-grown potted plants: About 2.4 cm to 4.6 cm. Wing diameter, shade house-grown potted plants: About 4.4 mm to 7 mm. Texture and luster, outer and inner surfaces: Smooth, glabrous; dull sheen. Wing color, shade house-grown potted plants: Outer surface: Close to N181D and 177B with stippling and streaks, close to 200B tinged with close to 147A. Inner surface: Close to N155D; colors and patterns from the outer surface are visible on the inner surface.

Inflorescence description:

*Inflorescence arrangement.*—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; jasmine-like with camphor note.

*Natural flowering season and flower longevity.*—Plants of the new *Caladium* typically flower during the spring and summer in central Florida; flowers develop about twelve weeks after growth commences; inflorescences last about three days before fading; inflorescences persistent.

*Spathe.*—Length, overall: About 7.2 cm. Length, distal open portion: About 4.6 cm. Length, proximal closed portion: About 2.6 cm. Width, distal open portion: About 2.6 cm. Depth, distal open portion: About 1.4 cm. Width, at constriction: About 1.1 cm to 1.2 cm. Width, proximal closed portion: About 2 cm. Shape, open portion: Elliptic, ovate. Apex: Acute to acuminate; apex hooked forward. Base: Obtuse to acute. Margin: Entire. Texture and luster, front surface: Smooth, glabrous; dull sheen. Texture and luster, rear surface: Smooth, glabrous; distally, dull and proximally, slightly glaucous. Color, front surface: Distal open portion: Close to N155D; margin, close to 56D; interveinal areas variably mottled with close to 185B; with subsequent development, distally becoming closer to 199C and 199D. Proximal closed portion: Close to 148D, distally, flushed with close to N186C; colors do not change with subsequent development. Color, rear surface: Distal open portion: Close to N155D; center, flushed with close to 159C and 159D; at the base, tinged with close to 147D; colors do not change with subsequent development. Proximal closed portion: Close to 147B; margins, close to 187C; colors do not change with subsequent development.

*Spadix.*—Length, overall: About 5.2 cm. Length, male flower zone (including sterile flowers): About 4 cm. Length, sterile zone: About 1.1 cm. Length, female flower zone: About 1.2 cm. Diameter, male flower zone: About 8 mm. Diameter, sterile flower zone: About 6 mm. Diameter, female flower zone: About 8 mm. Shape: Columnar, spindle-shaped. Apex: Acute. Base: Obtuse. Aspect: Upright. Color, mature, male zone: Close to 158D. Color, mature, sterile zone: Close to 155D. Color, mature, female zone: Stigmas, close to 159D; ovaries, close to 165D. Male flowers: Quantity per spadix: About 123. Shape: Obovate. Height: About 2 mm to 2.5 mm. Diameter: About 2.2 mm to 2.5 mm. Pollen amount: Abundant. Pollen color: Close to 11C. Female flowers: Quantity per spadix: About 132. Shape: Obovate. Height: About 2.5 mm. Diameter: About 1 mm to 1.2 mm. Stigma color: Close to 159D. Ovary color: Close to 165D.

*Scapes.*—Length: About 27.8 cm. Diameter: About 5 mm. Strength: Sturdy; flexible. Aspect: Mostly erect, straight. Texture and luster: Smooth, glabrous; glaucous and dull sheen. Color: Close to 181D and 177D with stippling and streaks, close to 200A and 200B; just below spathe, close to 148B and 182D with faint stippling and streaks, close to 200A and 200B tinged with close to 147B.

*Seeds and fruits.*—To date, seed and fruit development have not been observed on plants of the new *Caladium.*

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'BLB F-023' as herein illustrated and described herein.

* * * * *